(12) United States Patent  
Gerwin et al.

(10) Patent No.: US 6,979,124 B2  
(45) Date of Patent: Dec. 27, 2005

(54) IMAGE QUALITY VASCULAR UNIFORMITY EVALUATION METHOD AND APPARATUS

(75) Inventors: Paul J. Gerwin, Cincinnati, OH (US); Clarence R. Stueve, Lynnwood, WA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/364,277

(22) Filed: Feb. 11, 2003

(65) Prior Publication Data

US 2004/0156480 A1    Aug. 12, 2004

(51) Int. Cl.[7] .......................................... G01D 18/00
(52) U.S. Cl. ...................................... 378/207; 378/18
(58) Field of Search .................................. 378/18, 207

(56) References Cited

U.S. PATENT DOCUMENTS

| | | | |
|---|---|---|---|
| 3,887,804 A | | 6/1975 | Morgan et al. |
| 4,048,507 A | | 9/1977 | de Gaston |
| 4,055,771 A | * | 10/1977 | Goodenough et al. ........ 378/18 |
| 4,649,561 A | | 3/1987 | Arnold |
| 4,724,110 A | | 2/1988 | Arnold |
| 5,715,823 A | | 2/1998 | Wood |
| 5,745,268 A | | 4/1998 | Eastvold et al. |
| 6,076,966 A | | 6/2000 | Stueve |
| 6,200,025 B1 | * | 3/2001 | Rich ........................... 378/207 |
| 6,381,557 B1 | | 4/2002 | Babula |
| 2002/0114500 A1 | | 8/2002 | Faber et al. |

FOREIGN PATENT DOCUMENTS

| | | |
|---|---|---|
| EP | 0 874 536 A1 | 10/1998 |
| WO | WO 02/30283 A2 | 4/2002 |

OTHER PUBLICATIONS

A.R. Cowen, B.Sc., et al.; A set of X-ray test objects for image quality control in digital substraction fluorography. I: design considerations; The British Journal of Radiology, 60, Oct. 1987, 1001-1009.

A. R. Cowen, A Set of X-Ray Test Objects for image Quality Control in Digital Subtraction Fluorography, I: Design Considerations, The British Journal of Radiology, 1987, 60, 1001-1009, The University of Leeds, Department of Medical Physics, The General Infirmary, Leeds LS1 3EX.

* cited by examiner

*Primary Examiner*—Craig E. Church  
*Assistant Examiner*—Jurie Yun  
(74) *Attorney, Agent, or Firm*—Henry Policinski; Joseph S. Heino; Patrick M. Bergin

(57) ABSTRACT

A method and apparatus for providing an image quality test and reporting method for x-rays that allows a field engineer to effectively maintain and troubleshoot vascular imaging systems produced by all manufactures. In general, the method and apparatus of the present invention provides for a test stand, a plurality of x-ray test phantoms (10, 20, 30, 40, 50, 60, 70) and a computer program for data entry, analysis and storage of the test results.

21 Claims, 11 Drawing Sheets

IMAGE QUALITY VASCULAR UNIFORMITY EVALUATION METHOD AND APPARATUS

FIELD OF THE INVENTION

This invention relates generally to X-ray vascular imaging and to devices used for such imaging. More particularly, it relates to a reporting method and to an image quality apparatus that allows field service engineers to maintain and troubleshoot a wide variety of X-ray vascular imaging systems.

BACKGROUND OF THE INVENTION

In the area of X-ray vascular imaging devices, poor vascular image quality, non-standardized vascular image quality, and the inability to quantify and archive vascular image quality, are each a particular problem encountered by radiographic technicians and service engineers. The need to systematically measure the image quality of multiple vascular X-ray equipment systems dates back to the 1970's. Since then, a number of systems have developed. In the experience of these inventors, however, the method and apparatus of the present invention is the most versatile, all-inclusive, software-based program available in the industry.

BRIEF SUMMARY OF THE INVENTION

In the x-ray industry there is a wide variance of equipment specification. As a result, few field engineers are able to keep up with every type of x-ray machine across every manufacturer. There is also a lack of a general image quality standard among existing x-ray machines. Further, many of the existing testing methods are difficult to reproduce across machine types and over time with the same machine. Lastly, consumer confidence in x-ray machines has suffered because the industry lacks an accepted benchmark to compare all the machines against.

The method and apparatus of the present invention provides for a specific test stand that utilizes a number of calibration phantoms. This "Image Quality Vascular Uniformity Evaluation" (IQVUE) tool is used in the form of a kit that includes other devices necessary to measure and quantify vascular image quality. For example, an adapter is used to fix radiation probes to a test stand in precise positions during the testing process. A number of acrylic blocks and metal (aluminum and copper) plates are provided that fit securely within the test stand during the testing process. These blocks and plates act as X-ray beam attenuators. The kit of the present invention also includes a laminated lead blocker for blocking the X-ray beam as desired or required during testing. The kit includes a sizing phantom, a circle phantom and a dynamic range phantom, each of which provides unique x-ray beam attenuation objects for testing and measurements. A video test pattern generator is provided, as is a riser cage to perform fluoroscopic testing, a micro-viewer and a number of lead identification markers that are used to identify image intensifier size and source to image distance. Software is provided for use in conjunction with the kit to provide the means to analyze, display, report and archive the IQVUE data. The software guides the field service engineer through the procedure, provides various data entry fields and creates various reports and analyses based on the collected data.

The method and apparatus of the present invention provide multiple custom IQVUE video test patterns that are used to quantify resolution and linearity values of video monitors common to vascular systems, regardless of OEM. The present invention also provides for placement of phantoms in the IQVUE stand with means for table height adjustment to superimpose the opposing circles so as to achieve a standard source to input distance for any vascular imaging system. The present invention further provides for a noninvasive method for analyzing the vascular image quality. In other words, no equipment covers need be removed. The analysis tool permits optimization of the present invention through troubleshooting and problem isolation techniques.

The present invention further provides several valuable service tools to the field engineer. First, and extremely important in extended service contracts is the ability the IQVUE platform to provide pre-contractual evaluations of x-ray performance. Equally important is the benchmarking ability of the present invention. Without a uniform standard among x-ray machines it is impossible to compare machine performance. The method and apparatus of the present invention also serves a useful historical reference and enables more accurate prediction of when parts will need to replaced as opposed to waiting until failure and then replacing equipment.

The foregoing and other features of the method and apparatus of the present invention will be apparent from the detailed description that follows.

DETAILED DESCRIPTION OF THE INVENTION

Figure 1:
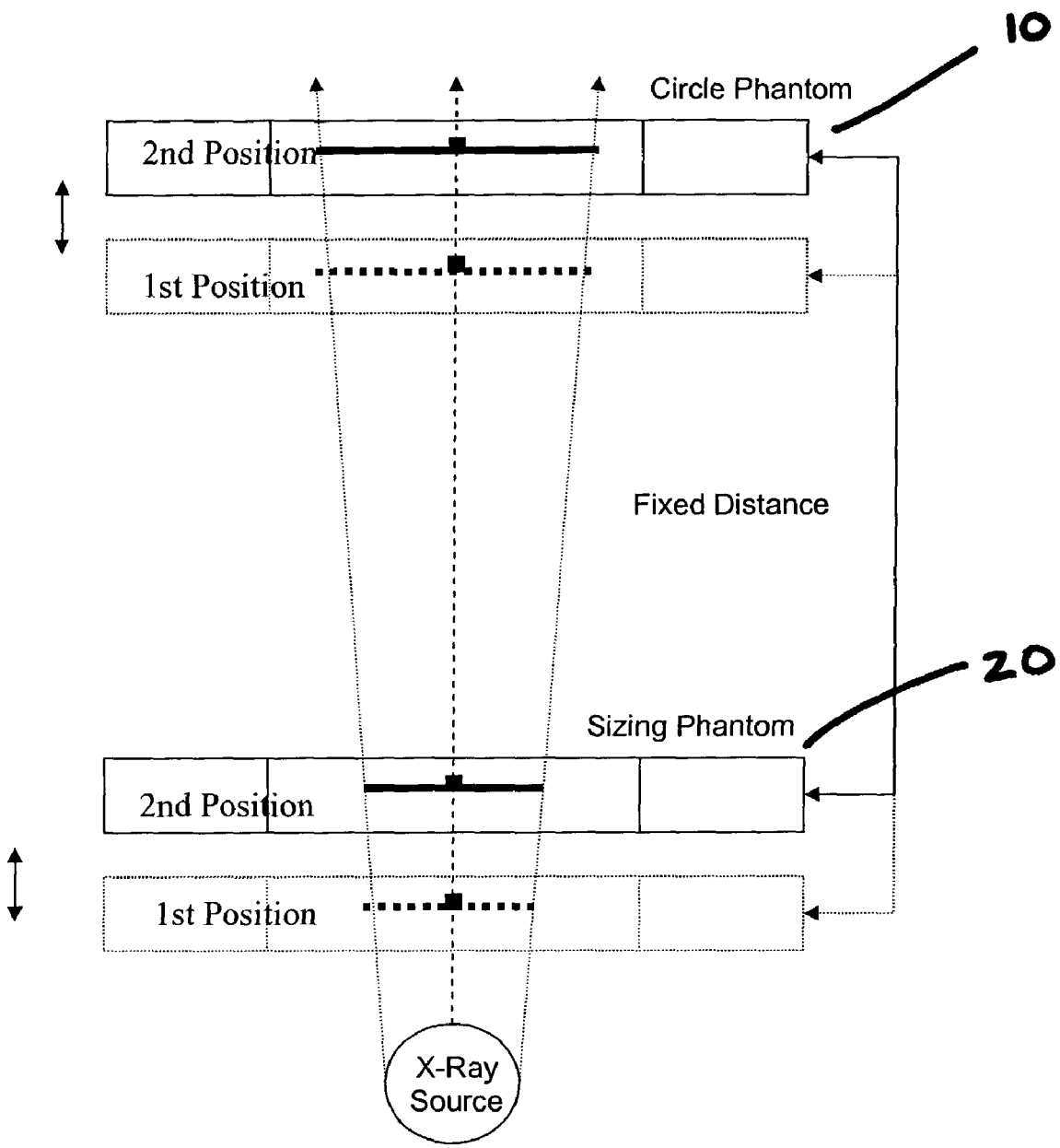
FIG. 1 is a schematic view of the geometric positioning test that is used to set a standard source to input distance in accordance with the present invention.
Figure 2:
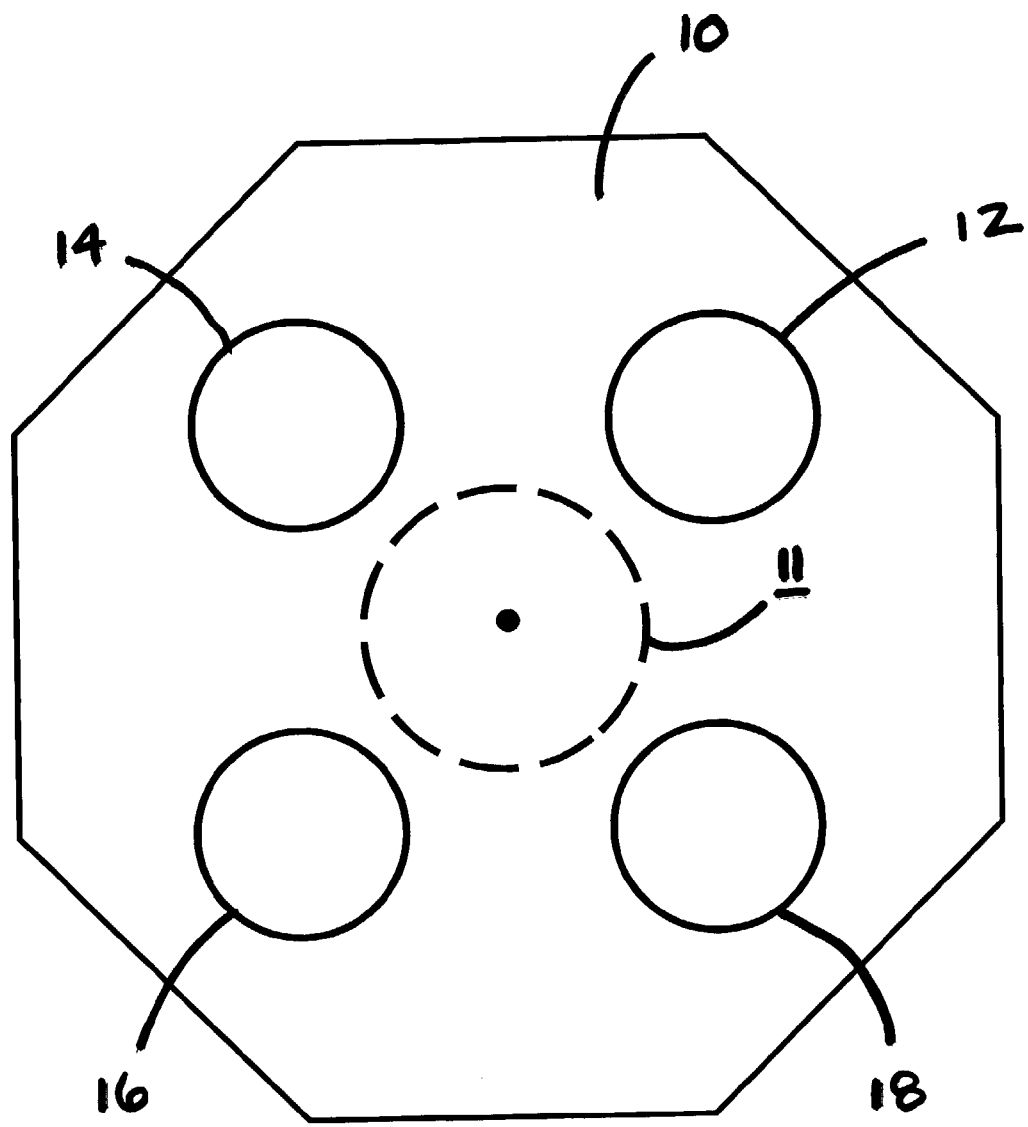
FIG. 2 is a schematic of the circle phantom used in the present invention.
Figure 3:
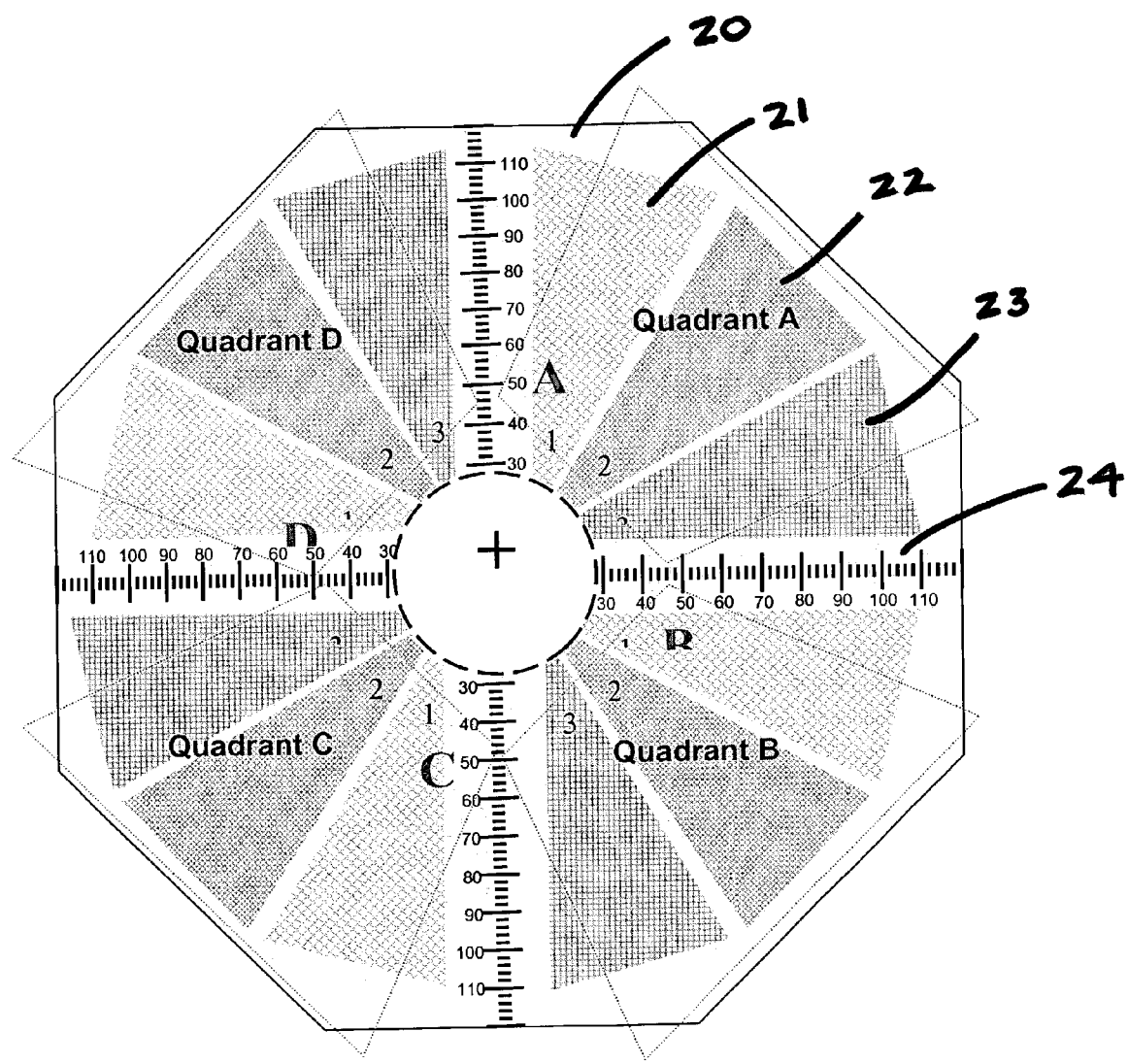
FIG. 3 is a schematic representation of the sizing phantom employed in the focus uniformity test.
Figure 4:
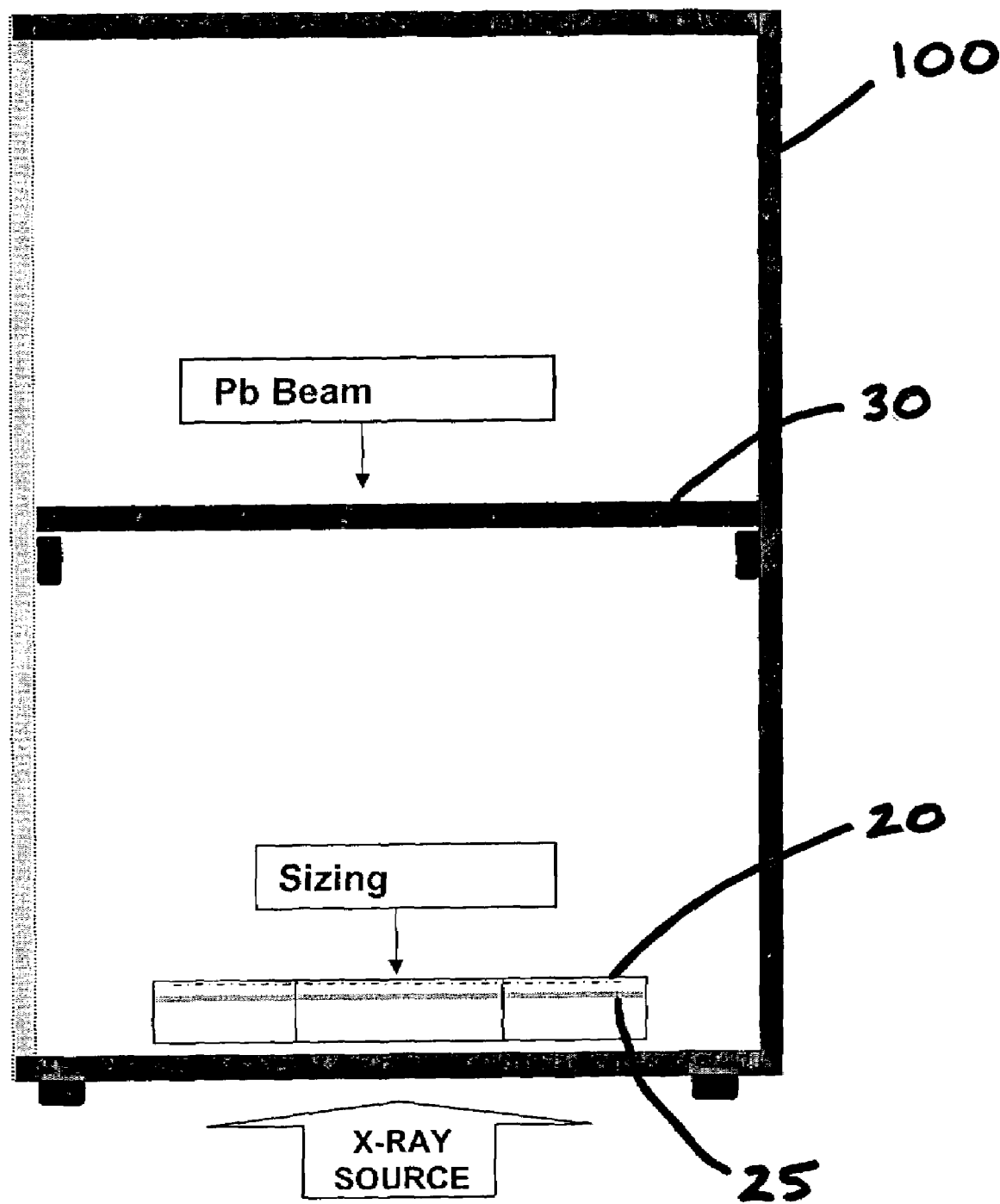
FIG. 4 is a schematic representation of the test stand employing a lead beam blocker in cooperation with the sizing platform and phosphorescent screen.
Figure 5:
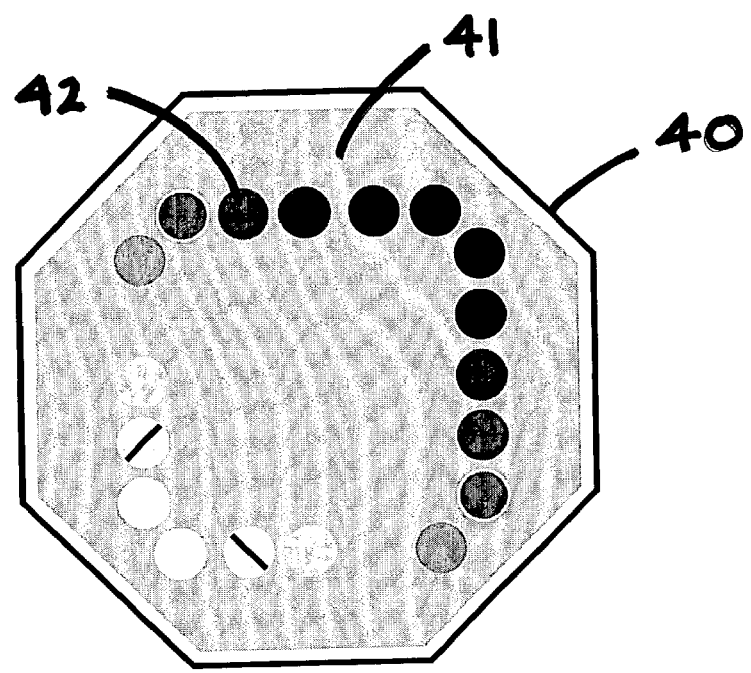
FIG. 5 is a schematic representation of the dynamic range phantom.
Figure 6:
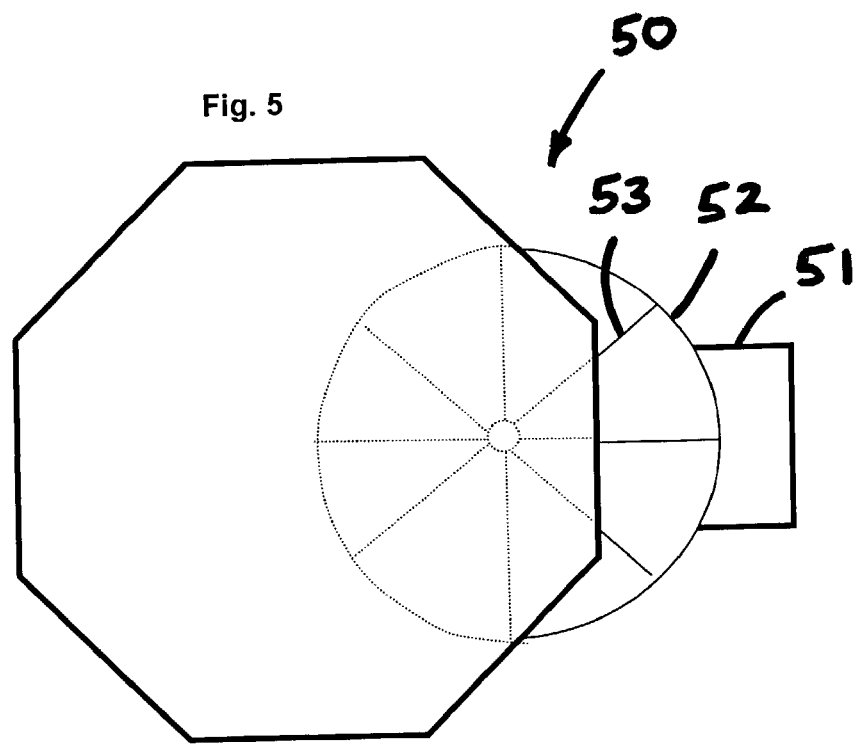
FIG. 6 is a schematic representation of the rotating spoke phantom.
Figure 7:
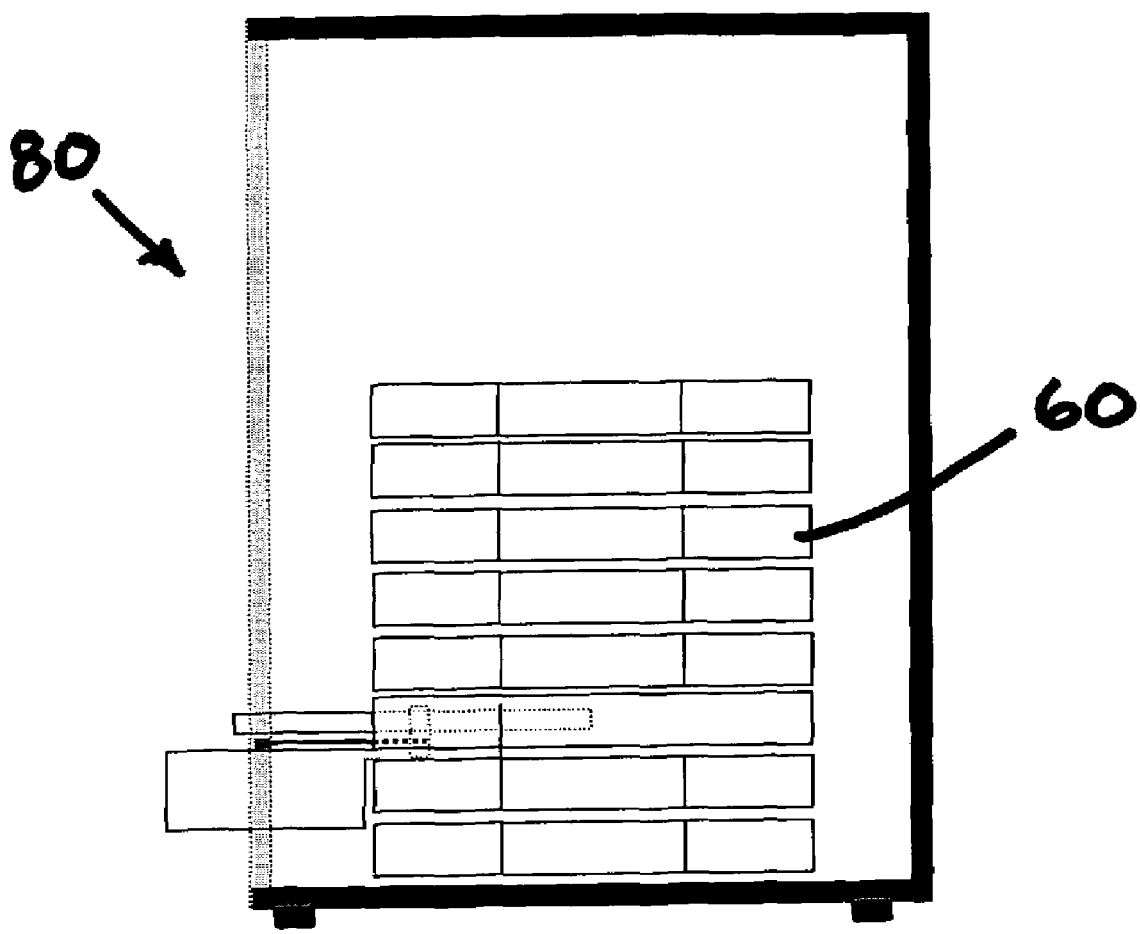
FIG. 7 is a schematic representation of the rotating spoke phantom as used in the IQVUE test stand.
Figure 8:
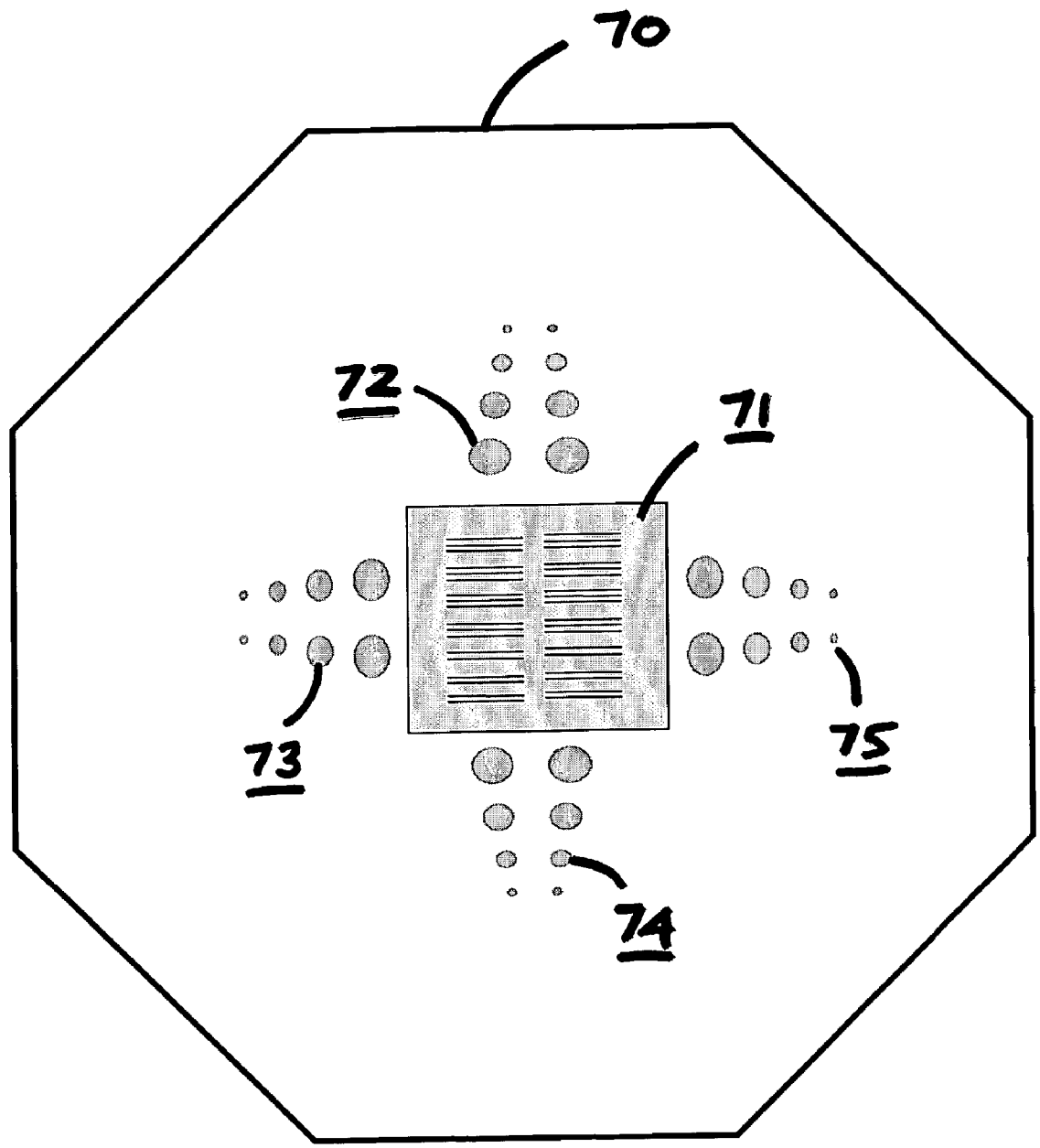
FIG. 8 is a schematic representation of the central plate phantom used to benchmark the spatial resolution, mag resolution low contrast detectability of an imaging system.
Figure 9:
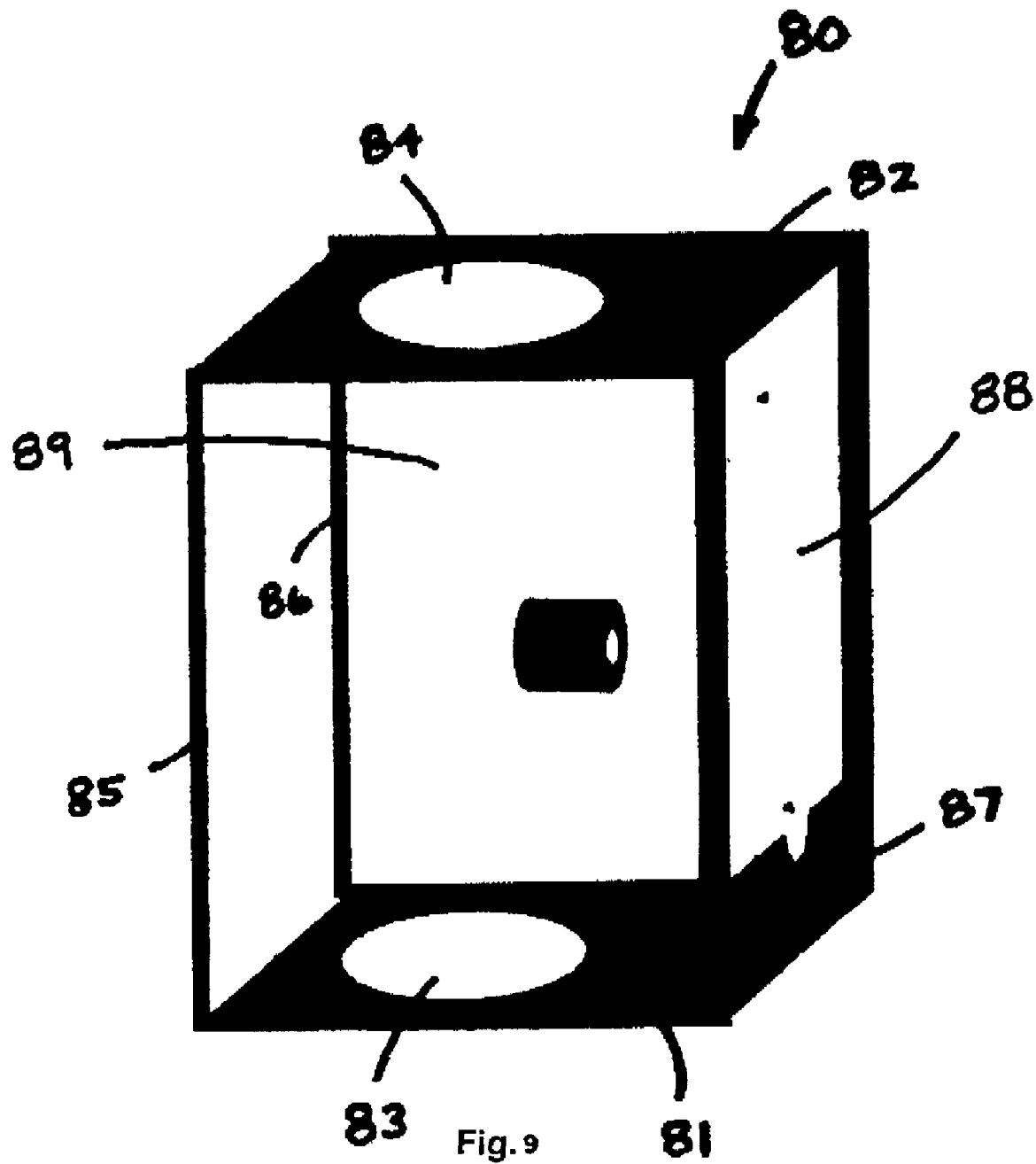
FIG. 9 is a schematic of the IQVUE test stand as used in the present invention.
Figure 10:
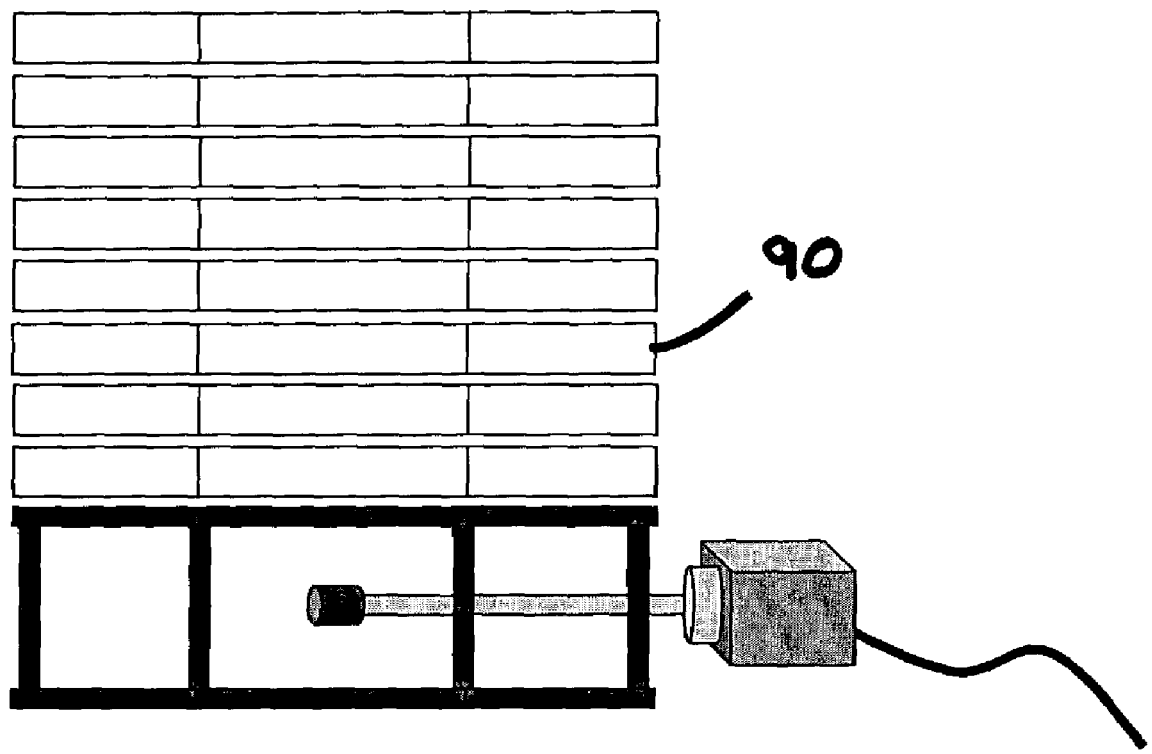
FIG. 10 is a schematic view of the riser cage having a radiation probe inserted within it.
Figure 11:
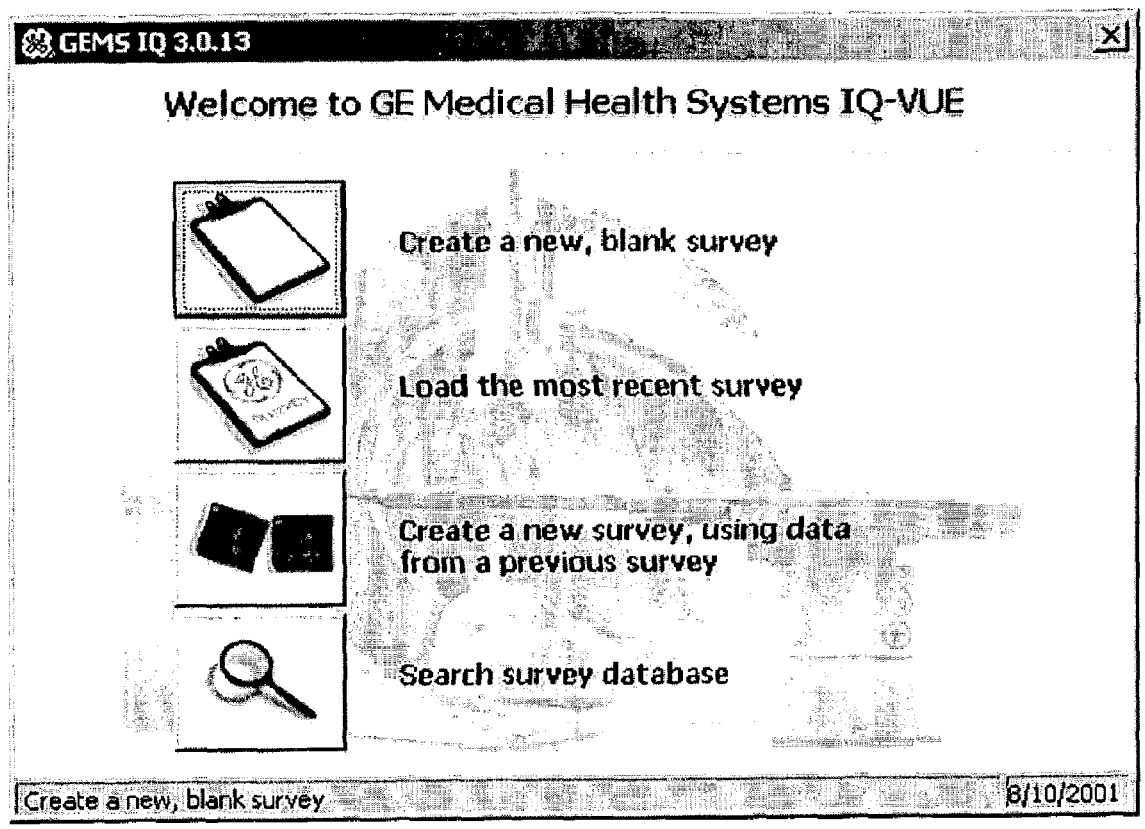
FIG. 11 is a screen display of the home screen of the IQVUE tool.
Figure 12:
FIG. 12 is a screen display used in the collimator performance test that shows both a series of instructions along the left hand side of the monitor and a survey sheet on the right.

Referring now to the drawings in detail wherein like reference numerals represent like elements throughout, FIG. 1 illustrates the various elements of the preferred embodiment of a kit that utilizes the apparatus of the present invention. The kit, generally identified 100, is designed to create an image quality tool and reporting method that allows a field service engineer to effectively maintain and trouble shoot vascular imaging systems across all manufacturers. As shown, the kit components include the following elements:

stand 80,
central plate 70,
half value layer kit,
lead beam blockers 30,
test pattern generator,
contrast phantom 40,
rotating spoke 50,
circle phantom 10,
sizing phantom 20,
acrylic beam attenuators 60,
copper and aluminum attenuators, and
various accessories.

The goal of the present invention is to provide a field engineer with an effective way to collect clinically relevant image quality data on any vascular imaging system. In this fashion, businesses can compare the image quality and radiation dose trends of a single system over time, one system to other systems in the same facility, or to various systems within a zone. The expected applications of the IQVUE tool described herein include early recognition of deteriorating image quality in acquisition and display equipment, improved long term image quality, enhanced customer satisfaction, reduced radiation exposure to patients and operators, and standardized image quality across an installed base. The IQVUE program includes the following test modes:

Monitor performance. The x-ray itself is not the only important part of the x-ray system. The performance of the monitor is also very important to accurate imaging. This test employs a test pattern generator to produce a special test pattern to establish that the monitor is performing properly, set the contrast and brightness of the monitor into the correct operating range and to record the gamma curve of the monitor output for later use in the dynamic range test.

Geometric positioning. When positioned in the test stand, the sizing phantom 20 and the circle phantom 10 allow the operator to obtain a calibrated standard distance that provides the ability to evaluate any cardiac or vascular imaging system under identical geometric conditions. The standard distance is obtained by raising or lowering the table top until a central 25 mm diameter circle in the sizing phantom 20 is exactly superimposed onto a 42.75 mm diameter central circle of the circle phantom 10. Once the standard distance is obtained, the IQVUE software is able to provide numerous data conversion calculations that compensate for equipment related variables.

Circle phantom. The circle phantom is used in the brightness uniformity test, among others, to measure the brightness in five areas of the x-ray field of view that are intended to produce a homogeneous image in the x-ray system, so that the operator can determine if the resulting image is uniform in brightness. The circle phantom 10 incorporates a center circle 11 and four outer circles 12, 14, 16, 18, placed in the 2, 4, 8 and 10 o'clock positions. When imaged fluoroscopically, the circles provide five specific locations where the brightness uniformity at the procedure room monitor is measured. The circle phantom 10 is also used with the sizing phantom 20 and the stand to set a standard source-to-input-distance (STD SID), which is used for most of the IQVUE tests.

Focus uniformity. The sizing phantom 20 is divided into quadrants. A composite pattern of three groups of copper screens, the first having 40 holes per inch 21, 60 holes per inch 22, and 80 holes per inch 23 is embedded in a radial alignment within each quadrant. When imaged, the visibility of the various copper screens (or mesh) allows the documentation of the finest mesh in each quadrant, and also if the monitor focus is uniform across the visible image.

Image sizing. The field of view size accuracy is a simply a test that verifies whether the x-ray's field of view is within expected design parameters. The sizing phantom 20 incorporates a four quadrant lead ruler 24. The 20 to 110 mm ruler 24 features reticules in 2 mm increments. When imaged radiographically on the procedure room monitor, the ruler 24 provides the ability to accurately document the field-of-view sizes of any cardiac or vascular imaging system, from 10 to 40 cm.

Collimator performance. The collimator performance test is government mandated test to verify that the x-ray tube collimator is limiting the size of the x-ray beam to the image intensifier field of view. The sizing phantom 20 incorporates a four quadrant lead ruler 24. The 20 to 110 mm ruler 24 features reticules in 2 mm increments. When imaged radiographically on the procedure room monitor, the ruler 24 provides the ability to accurately document the position, alignment and functionality of the X-ray shutter assembly. An X-ray sensitive phosphorescent screen 35 embedded in the sizing phantom, under the 4 quadrant lead ruler 24, allows the ability to accurately document the position, size and alignment of the X-ray beam.

System Dynamic Range. The dynamic range test measures the monitor density of two sets of 10 "pills" 42 of graduated densities that are placed in the x-ray beam in a special phantom. These density measurements are then adjusted using an algorithm based on the gamma curve measurement taken in the monitor performance test. This adjustment is performed to eliminate the influence of the monitor CRT variances and give a true representation of the dynamic range of the system.

The dynamic range, or contrast phantom 40 is comprised of two groups of ten "pills" 42 embedded into a $\frac{1}{8}^{th}$ inch copper plate 41 positioned in a square matrix around a central area. When imaged radiographically, the "pills" 42 provide a 10 step gray-scale pattern on the procedure room monitor, which is measured with a calibrated light meter. The "brightness" values recorded by the light meter provide a gamma curve that is modified by a dynamic range monitor correction algorithm that is used to subtract the monitor gamma.

A computer program is the used to obtain the appropriate grayscale level corresponding to a given measured screen luminance. The computer program requires implementation of a third degree polynomial curve fit to the measured screen luminance values using a least squares curve fit to produce the coefficients for the powers of x.

Rotating Spoke. The rotating spoke object 50 provides a visual evaluation of wire size visibility, motion unsharpness and the effects of digital temporal averaging algorithms. The device consists of a housing 51, a rotatable acrylic disk 52, (test object) and five stainless steel wires of varying diameters. The present invention employs stainless steel wires having diameters of 0.022 in, 0.016 in., 0.012 in., 0.009 in., and 0.005 in. The rotating spoke phantom 52 is placed within a 20 cm thick acrylic attenuator 60 and is fluoroscopically imaged in the 6 or 7 inch field of view (FOV). The rotating spoke phantom 50 is first evaluated while stationary and then again while rotating at 30 revolutions per minute (rpm).

Benchmark. The central plate phantom 70 incorporates a centrally positioned LP/mm spatial resolution test object around which is positioned a series of holes 72, 73, 74, 75 with different diameters and depths. The holes are filled with elemental iodine dispersed in epoxy. The concentrations of iodine in each pattern 72, 73, 74, 75 are 200, 100, 50 and 25 mg/cc, respectively. When imaged radiographically within a stack of seven 2.5 cm thick acrylic attenuators 60, the central plate phantom 70 is used to benchmark the spatial resolution, low contrast detectability and generator performance of any cardiac or vascular imaging system.

Spatial Resolution. The spatial resolution test is designed to verify that the image intensifier and optical focus is correct and that images coming from the system have adequate detail. The central plate phantom 70 incorporates a centrally positioned (0.5–5 LP/mm) spatial resolution test object. Initially, a magnified spatial resolution test is done by radiographically imaging the central plate phantom 70 placed in the middle of a stack of seven 2.5 cm thick acrylic attenuators 60 within the IQVUE test stand. A more typical spatial resolution test is done by placing the central plate phantom 70 on top of the IQVUE test stand 80, next to the anti-collision device, and removing all the acrylic attenuators 60 from the x-ray beam.

Low Contrast Detectability. The low contrast detectability test is used to verify whether the video system is able to demonstrate small, low contrast objects and that the lag period between the video pickup and the video is acceptable. The central plate phantom 70 incorporates four patterns of eight holes 72, 73, 74, 75 each positioned around a centrally located LP/mm spatial resolution phantom 71. The eight holes in each pattern have different diameters and depths that are filled with elemental iodine dispersed in epoxy. The concentrations of iodine in each pattern 72, 73, 74, 75 are 200, 100, 50 and 25 mg/cc, respectively. When imaged radioagraphically within a stack of attenuators, the central plate phantom 70 provides the opportunity to quantify the low contrast detectability of any cardiac or vascular imaging system.

IQVUE Test Stand. The test stand 80 is used to set and maintain geometric positions of various phantoms, radiation probes, acrylic attenuators, HVL filters and Source to Input Distance (SID) or relationships of cardiac and vascular imaging systems. Its use allows uniform and consistent collection of data as well as significantly reducing the time required to complete the IQVUE evaluation. The test stand 80 can be used in the AP plane position and, if necessary, the cross-table LAT position. When positioned within the test stand 80, the sizing 20 and circle phantoms 10 allow the operator to set a calibrated standard SID, providing the ability to evaluate any cardiac or vascular imaging system under analogous geometric conditions. Once this standard is set, the IQVUE software provides multiple data conversion calculations that compensate for equipment related variables.

The IQVUE test stand 80 is, in general, rectangular in shape and has a base 81 having an octagonal aperture 83 defined within it. The test stand 80 also has a top 82 having an octagonal aperture 84 defined within it, a first support 85, a second support 86 and a back wall 87 having a plurality of apertures 88, 89 for the placement of phantoms and other test equipment. Of course, the test stand 80 could be configured or constructed in many shapes and sizes and that recited is intended to embody the spirit of the invention and not the exact structure.

Riser Cage. The riser cage allows the quantification of the typical fluoroscopy exposure rate (the California 5R/minute test.) The riser cage provides a platform onto which eight 2.5 cm. thick acrylic attenuators 60 may be placed. The center of the radiation probe is positioned within the riser cage, 25 mm below the acrylic attenuators. This configuration produces scatter radiation similar to that encountered in patient examinations. The typical fluoroscopy exposure rate test is similar to the old "tabletop dose" test.

The apparatus of the present invention also measures the table pad absorption factor. In general, table pads used with cardiac imaging systems should not absorb more than 7% of the x-ray beam. The apparatus also performs the half value layer test which is mandated by federal and state laws. In general the test is used to measure and verify that there is an adequate amount of inherent filtration in the x-ray beam to limit "soft" radiation, or low energy x-rays to the patient.

Lastly, the device of the present invention provides for a test to verify the cine image density provided by the automatic brightness control system. The cine image density should be essentially the same in each field of view and should be compatible with the light output of the cine projector.

It will be appreciated by those skilled in the art that the tests described above are not an exhaustive list and that additional tests can be performed using the test stand according to the method and apparatus of the present invention. It should also be clear that a plurality of acrylic attenuators 60 have been provided to simulate patients of all shapes and sizes in all of the tests provided.

The present invention also utilizes a new and unique software program to display, analyze, report and archive the data gathered from one or more of the above described tests. The software is designed to guide the operator through the procedure, provide data entry fields and create various reports and analysis based on the collected data. The software components include various functionalities, including:

test formats,
an equipment configuration wizard,
equipment setup/radiographic parameters selections,
test suites with incorporated sub tests,
electronic and paper data entry fields,
reports,
dynamic database,
database administration,
continuous and discrete procedure formats,
email functionality, and
links to an online user guide.

In application, the software program used in conjunction with the method and apparatus of the present invention provides several options including the options of searching a database of surveys, creating a new survey, and loading a recent survey. The user is then prompted to enter the system's ID code. A configuration tool is provided if the system ID number is not available. The configuration tool, or ID code, is then used to configure the software to indicate test equipment, field engineer data, input values, data location and system parameters. The user is then able choose the type and number of tests to perform. The software provides a complete IQVUE survey, user selectable groups of surveys or predefined task groups. The software of the present invention then provides input screens for prompting the user to enter information such that the user performs the test in an accurate sequence. Help links are provided with many of the input parameters so that, if the user is unfamiliar with a particular machine, the information can be retrieved from a database of information. A report creator is also offered. The report creator provides multiple report formats and simple, one button operation.

The system configuration option provides several tabs for several data fields, including facilities, groups, labs, lab contacts, and field engineers. Thus, the field engineer can begin by selecting a facility, then a lab and get all of the information about a particular machine in a simple, easy to use format. After verifying the information on the screen, the field engineer can click "OK." The software then configures itself to prompt the user for the appropriate system information.

Once the software is configured for the systems, the user is presented with a menu having survey, parameters, tests and reports option. The IQVUE test suite offers several different tests including tests for monitor performance, spatial resolution, low contrast detectability, dynamic range resolution, collimator congruency, image receptor field size, focus uniformity, brightness uniformity, dynamic range testing, x-ray tube performance, fluoroscopy and dose level, maximum radiation, digital and non digital, benchmarking, and custom testing.

The test input screens provide data entry fields for the field engineer, instructions for operating the machine and set up instruction for the field engineer. They also provide a series of notes that are useful to the field engineer in testing the machine as well as links to help files that provide information pertinent to the machine being tested. The data entry fields also provide space for the entry of comments.

Lastly, the software utilized with the method and apparatus of the present invention provides a reporting function that creates a physicist report, a service report, a customer report and an equipment report, each obviously providing data intended for a different audience. The reporting function permits the field engineer to browse among saved reports and to email reports. The software also features an update capability, an internal, upgradeable database that provides information for updating of OEM equipment and performance characteristics.

The IQVUE invention provides the field engineer with an effective way to collect clinically relevant image quality data on any vascular imaging system so that a business can compare the IQ and radiation dose trends of a single system over time, or one system to other systems. Specifically, the IQVUE tool provides for early recognition of deterioration image quality in acquisition and display equipment, improved long term image quality, enhanced customer satisfaction, reduced radiation exposure to the patient and the operator and standardized image quality across installed machines.

PARTS LIST 10 circle phantom
11 center circle of circle phantom
12 two o'clock circle of circle phantom
14 ten o'clock circle of circle phantom
16 eight o'clock circle of circle phantom
18 four o'clock circle of circle phantom
20 sizing phantom
21 40 hole per inch screen
22 60 hole per inch screen
23 80 hole per inch screen
24 four quadrant lead ruler
25 phosporescent screen
30 lead beam blocker
40 dynamic range phantom
41 copper plate of dynamic range phantom
42 pills
50 rotating spoke phantom
51 housing
52 rotatable acrylic disk
53 wires
60 riser cage
70 central plate phantom
71 central test object
72 200 mg/cc iodine deposit
73 100 mg/cc iodine deposit
74 50 mg/cc iodine deposit
75 25 mg/cc iodine deposit
80 IQVUE test frame
81 base of test frame
82 top of test frame
83 aperture in base
84 aperture in top
85 first support
86 second support
87 back wall
88 first back wall aperture
89 second back wall aperture
90 acrylic beam attenuators

What is claimed is:

1. An apparatus for use in evaluating the image quality of an x-ray machine comprising:a base:
   an aperture defined within said base;
   a plurality of supports rising upwardly from said base;
   a plurality of test objects to evaluate the image quality produced by an x-ray machine, one of said test objects being a circle phantom having a center circle and four outer circles arranged uniformly around the center circle;
   a wall rising upwardly from said base, said wall providing a plurality of apertures for inserting test objects;
   a top; and
   an aperture defined within said top for accepting test objects.

2. The apparatus of claim 1 wherein one of said test objects is a sizing phantom, said sizing phantom divided into quadrants wherein each quadrant is further divided into three pads, each of said parts having a pattern of copper screens of differing mesh sizes.

3. The apparatus of claim 2 wherein the sizing phantom further includes a four quadrant lead ruler in 2 millimeter increments.

4. The apparatus of claim 3 wherein a phosphorescent screen is embedded into the sizing phantom.

5. The apparatus of claim 4 wherein a lead beam blocker is installed above the sizing phantom to amplify the x-ray exposure.

6. The apparatus of claim 5 wherein one of the test objects is a dynamic range phantom having a plurality of pills embedded into a thin copper plate.

7. The apparatus of claim 6 wherein one of the test objects is a rotating spoke phantom comprising:
   a housing;
   a rotatable acrylic disk;
   a plurality of stainless steel wires of varying thicknesses either embedded into or attached to the acrylic disk;
   a acrylic attenuator;
   wherein the rotatable disk can be imaged while both stationary and rotating.

8. The apparatus of claim 7 wherein one of the test objects is the central plate phantom comprising a central plate surrounded by a plurality of holes in a variety of different sizes, said holes being filled with elemental iodine.

9. The apparatus of claim 8 wherein a user of the test objects is prompted by a computer-readable memory to enter certain test results and, upon entry, the computer stores, displays and analyzes the result.

10. For use in evaluating the image quality of x-ray machines of different manufacture, a test device that comprises:
 a base, said base having an aperture defined within it;
 a plurality of support members extending generally upwardly from the base;
 a plurality of test objects comprising:
  a circle phantom, the circle phantom having a center circle and four outer circles arranged uniformly around the center circle;
  a sizing phantom, said sizing phantom being divided into specific parts having screens with different mesh sizes;
  a dynamic range phantom, said dynamic range phantom being comprised of a plate having a plurality of pills corresponding to a stepwise gray scale;
  a central plate phantom having a plurality of radioactive objects in different sizes and depths; and
  a rotating spoke phantom, said rotating spoke phantom providing a plurality of differently shaped wires to rotate beneath the x-ray;
 a wall rising generally upwardly from the base, said wall having a plurality of apertures defined within it for inserting test objects therein; and
 a top, said top having an aperture defined within it for accepting test objects.

11. The test device of claim 10 wherein each phantom produces a machine test survey and a computer-readable memory prompts the user- to record the values measured in each survey the computer-readable memory than storing and analyzing the values entered.

12. A method for improving x-ray image quality comprising the steps of:
 creating a x-ray image survey using an x-ray machine, the x-ray image survey comprising the steps of evaluating the image quality of an x-ray of several known phantoms including a central plate phantom, a contrast phantom, a rotating spoke phantom, a circle phantom, a plurality of acrylic beam attenuators; and a sizing phantom;
 recording the results of the survey;
 providing a computer-readable memory having a database of information relating to x-ray machines of known manufacture for data analysis of the x-ray image survey, said computer-readable memory providing the applicable x-ray system parameters for the x-ray machine; and
 providing a data reporting step generating a pregenerated report format.

13. The method of claim 12 wherein the computer-readable memory provides data for x-ray machines of known manufacture and the data is accessed by product number of the machine.

14. The method of claim 13 wherein the computer-readable memory prompts the user to perform specific tests based on the type of x-ray machine given, prompts the user to perform the test and obtain the data and provides several types of data entry fields.

15. The method of claim 14 wherein the computer-readable memory is capable of generating a plurality of different reports such as physicist's report, an engineer's report, a customer report and an equipment report.

16. A method for improving x-ray image quality comprising the steps of:
 providing a test stand having a plurality of apertures for placement of phantoms;
 providing a computer-readable memory having a database of information relating to x-ray machines of known manufacture, wherein said database further provides standard x-ray parameters, wherein said database further provides a test format corresponding to each of said x-ray machines of known manufacture, wherein said computer-readable memory also provides a data entry platform and a report generating platform;
 providing a plurality of phantoms wherein each of said phantoms is employed for creating one or more image surveys using an x-ray machine of known manufacture the plurality of phantoms comprising a central plate phantom having a plurality of radioactive objects of different sizes and depths; a contrast phantom; a rotating spoke phantom; a circle phantom having a center circle and four outer circles arranged uniformly around the center circle; a plurality of acrylic beam attenuators; and a sizing phantom; and
 wherein the computer-readable memory, test stand and phantoms can be used to test a broad range of x-ray machines of known manufacture.

17. The method of claim 16 wherein the test stand is comprised of a base, an aperture defined within said base, a plurality of supports rising upwardly from said base, a plurality of phantoms, a wall rising upwardly from said base, said wall providing a plurality of apertures for inserting phantoms, a top, and an aperture defined within said top for accepting phantoms.

18. The method of claim 17 wherein said computer has a configuration tool, said configuration tool prompting a user for a system identification code and if the system identification code is not available, said configuration tool prompting the user for information helpful to identifying the x-ray machine.

19. A method for improving vascular image quality comprising the steps of:
 providing a test stand that accommodates different x-ray machine designs,providing a plurality of phantoms for use with the test stand, said phantoms including, but not limited to:
 a central plate phantom, said central plate phantom having a plurality of radioactive objects in different sizes and depths;
 a contrast phantom, said contrast phantom being comprised of a plate having a plurality of pills corresponding to a stepwise gray scale;
 a rotating spoke phantom, said rotating spoke phantom providing a plurality of differently shaped wires to rotate beneath the x-ray;
 a circle phantom, the circle phantom having a center circle and four outer circles arranged uniformly around the center circle;
 a lead beam blocker;
 a dynamic range phantom, said dynamic range phantom being comprised of a plate having a plurality of pills corresponding to a stepwise gray scale;
 a plurality of acrylic beam attenuators;
 a sizing phantom said sizing phantom being divided into specific parts having screens with different mesh sizes; and
 providing a computer-readable memory having a configuration wizard for identifying particular x-ray machines, a variety of surveys for evaluating image quality and instruction for using the test stand and phantoms for evaluating image quality.

20. The method of claim 19 wherein the computer readable memory further includes data entry fields, links to online help, and instructions for using the x-ray machine.

21. The method of claim 20 wherein the test stand is comprised of a base, an aperture defined within said base, a plurality of supports rising upwardly from said base, a plurality of test objects, a wall rising upwardly from said base, said wall providing a plurality of apertures for inserting test objects, a top, and an aperture defined within said top for accepting test objects.

* * * * *